United States Patent [19]

Dulman

[11] Patent Number: 4,957,367
[45] Date of Patent: Sep. 18, 1990

[54] INTEFEROMETRIC IMAGING SYSTEM

[76] Inventor: Lev Dulman, 2366 33rd Ave., San Francisco, Calif. 94116

[21] Appl. No.: 200,574

[22] Filed: May 31, 1988

[51] Int. Cl.$^5$ ............................................. G01B 9/02
[52] U.S. Cl. ................................... 356/359; 356/394
[58] Field of Search ............... 356/352, 358, 359, 360, 356/394

[56] References Cited

U.S. PATENT DOCUMENTS

| | | | |
|---|---|---|---|
| 3,659,950 | 5/1972 | Troll et al. | 356/394 |
| 4,188,122 | 2/1980 | Massie et al. | 356/349 |
| 4,218,142 | 8/1980 | Kryger et al. | 356/394 |
| 4,389,669 | 6/1983 | Epstein et al. | 356/394 X |
| 4,421,410 | 12/1983 | Karasaki | 356/394 X |
| 4,627,733 | 12/1986 | Wada | 356/359 |

*Primary Examiner*—Davis L. Willis
*Assistant Examiner*—Matthew W. Koren
*Attorney, Agent, or Firm*—Clifton L. Anderson

[57] ABSTRACT

A quality control system provides for real-time, high-speed, high-resolution, comparison of the three-dimensional form of a sample with that of an examplar. The quality inspection system includes a sample analyzer, an exemplar analyzer, a comparator, a controller and a position memory. The sample analyzer includes a sample imager for providing an interferometric image of a sample of inspection, a sample scanner for scanning the sample image, and a sample transducer for converting the resulting sample scan into a sample signal representing the three-dimensional form of the sample. The exemplar analyzer similarly includes an exemplar imager, an exemplar scanner and an exemplar transducer to provide an exemplar signal representing an exemplary three-dimensional form for said sample. The comparator provides a comparison signal which identifies the scan times during which differences between the sample signal and the exemplar signal are detected. These signal differences correspond to differences in the fringe patterns of the interferometric sample and exemplar images and thus in form discrepancies in the sample from the exemplar. The comparison signal is used to enable writes to a memory which is constantly receiving position data at its data port so that position data corresponding to signal differences are stored. The position memory can then be read by a host system which can thus acquire a list of locations of potential defects.

12 Claims, 9 Drawing Sheets

INTEFEROMETRIC IMAGING SYSTEM

BACKGROUND OF THE INVENTION

The present invention relates to quality inspection systems and, more particularly, to automated quality inspection systems using comparative interferometric imaging.

The present invention is chiefly concerned with quality inspection in the manufacture of integrated circuits, although it has many other applications. Quality inspection is that aspect of quality control that deals with the detection of defects in products, usually during or upon the completion of manufacturing. Integrated circuits are typically fabricated in batches on crystalline wafers. At least some quality inspection procedures occur while the integrated circuits are still on the wafer to save the time and expense of dicing and packaging defective devices.

Two important and complementary quality inspection approaches are testing and visual inspection. Testing can be done by successively interfacing each die on a wafer with a test probe which applies test vectors, i.e., series of electrical inputs, and examining the resulting outputs. Testing determines whether an integrated circuit can do what it is designed to do and thus has high validity as a quality inspection procedure. The disadvantages of testing are that it is expensive and time consuming. More important from a developmental perspective, it can only be applied very late in the manufacturing process, generally not until integrated circuit fabrication is complete. Limited to testing, an integrated circuit manufacturer would be forced to complete and test an integrated circuit or entire wafer which was fatally defective due to early steps in the manufacturing process.

Visual inspection can be an effective complement to testing in that it can be applied at different manufacturing stages and serve to winnow out obviously defective circuits and wafers, savings further processing and testing expenses and providing more useful feedback as to the causes of defects. Visual inspection of integrated circuits generally employs human vision for at least part of the quality inspection process.

Two important advantages of human vision are its ability to recognize patterns and identify small deviations therefrom and its ability to distinguish depth in a two-demensional image of a three-dimensional object. The limited resolution of human vision can be compensated by magnifying the objects to be examined. However, fatigue and boredom are disadvantages of human vision that are not easily overcome. As a result, it is difficult to ensure that a human inspection is thorough and it is difficult to maintain even relatively good performance over repeated inspections.

Machine vision can be used to automate the inspection process and overcome the problems with fatigue and thoroughness that plague quality inspection systems that rely solely on human vision. Charge-coupled devices (CCDs) can be used to provide digitized images of an object for computer analysis. However, the amount of information and processing power and the sophistication of algorithms required to analyze a CCD image of an integrated circuit as effectively as a human have, heretofore, severely limited the effectiveness of automated machine-vision in quality inspection systems.

The main problem with machine vision in which CCD images are computer analyzed is the difficulty of determining depths represented in two-dimensional images. Humans can recognized depth using to shadow patterns as cues. However, such recognition requires distinguishing spatial variations in image intensity due to shadows from such variations due to reflectivity. Generally, computers cannot perform this function, although with very careful control of illumination some facility at interpreting depth can be attained with sufficiently sophisticated algotithms.

Even with the proper algorithms, machine depth perception is slow due to the tremendous amount of data that needs to be processed. An integrated circuit image can include tens of millions of individual pixels. Each pixel must be characterized with sufficient intensity, i.e.,"grey-scale", resolution for analysis so that multiple bits are required to characterize each pixel. While data compression techniques can be applied to images, these become less effective with increasing grey-scale differentiation.

Compounding the problems with machine depth perception and the data deluge is the relative inability to recognize patterns and small deviations therefrom using computer analysis of a digital image. Computers offset this with the ability to compare of information required for analysis. Thus, a computer can digitally process two images so as to highlight only the differences between them. Where the two images are of a sample and its exemplar, these differences indicate potential defects. Human vision can then complement the analysis by examining the relatively few points where discrepancies are indicated.

The biggest problem with comparing CCD images is that a valid comparison requires virtually identical lighting. Two images of a single object with many features having depth taken under illumination from slightly different directions would yield a comparison image showing many differences. The simplest method of eliminating problems with angles of illlumination is to provide even illumination of the objects to be imaged. This, however, has the effect of eliminating shadows and thus depth information from the image. This may be desirable if only reflectivity information is of interest, but is counterproductive where three-dimensional quality inspection is concerned.

Very rapid comparisons of a sample and an exemplar can be made holographically. For example, a positive holograph can be made of a sample and a negative of the exemplar. The holographic images can then be superimposed so that identical regions cancel; areas of non-cancellation represent potential defects. Holography does provide the more desirable three-dimensional form data for quality inspection. This holographic approach is attractive in that alignment is easily adjusted (until a best match between the holographs is apparent), processing is parallel and the result is human readable. The main disadvantage is that while the comparison is fast, preparation for the comparison involves making a holograph for each sample; this is cumbersome, especially when large numbers of samples are involved. There is also loss of information in the double transfer of information, i.e., from object to film and then from film to image for comparison. Also, the procedure requires that holographic supplies be stocked and expended which is costly and inconvenient. Finally, holographic information is not readily reducible to digital form for computer analysis.

There is another fundamental problem with using holographic comparisons-they are hard to make when there is no actual exemplar. Humans usually do not need exemplars because they can identify features that "look wrong". The reflectivity pattern that a sample is suppose to have can be generated, at least theoretically, from a knowledge of the layout and materials used to fabricate the sample. However, it is much more difficult to generate a holographic image of an integrated circuit from its layout. Hence, quality inspection systems using holographic comparaisons are limited to comparing samples with real exemplars.

The foregoing background suggests improvements to be pursued in advancing the art of quality inspection. A primary objective is the ability to extract three-dimensional data about a sample and to provide for comparisons with the form of an exemplar, whether the exemplar is a real object or a model. Speed is also important; quality inspection can involve checking very large numbers of samples, and each sample may be inspected many times during it manufacture. Preferably, one should neither stop to make holographic images of each sample nor have to store and manipulate huge amounts of data to determine defect locations on a sample. This also suggests that defect data should be provided in a compact format. Improved resolution is desired to reduce the magnification and viewing time required to analyze an integrated circuit.

SUMMARY OF THE INVENTION

In accordance with the present invention, the foregoing objectives are attained in a quality inspection system which compares interferometric images. The quality inspection system includes a sample analyzer which includes a sample imager and a sample image converter. The sample image converter includes a sample scanner for providing a sample scan by scanning the interferometric sample image. The sample image converter can also include a sample transducer to convert the optical scan into an electrical sample signal.

Normally, an interferometric sample image is constituted by an interference pattern superimposed on a normal sample image. The interference pattern includes dark curves called interference fringes which represent height changes in units of one-half the wavelength of the illumination source. A closed loop reflectivity filter can be included to minimize the contribution of the sample's reflectivity distribution to the interferometric sample image to make the interference lines more distinct. The interferometric sample image is thus like a contour map of the sample. Scanning converts the contour map into an optical signal of time-varying intensity, with dark instances corresponding to the scan of a contour fringe. The time-varying intensity is converted by the sample transducer to an electrical signal, so that, for example, it is voltage rather than intensity that varies over time.

The quality inspection system includes a comparator for comparing the sample signal with an exemplar signal. The exemplar signal can be obtained in parallel with the sample signal using an exemplar analyzer which is functionally the same as the sample analyzer. Alternatively, the exemplar signal can be a "playback" of an exemplar signal generated using the exemplar analyzer and recorded for later transmission in synchronism with the scan of the interferometric sample image. Also, the exemplar signal can be generated from a computer description of the design for the sample. In this case, the exemplar is considered "virtual".

The comparator provides a comparison signal indicating when the sample signal and exemplar signal are different. The quality inspection system includes a controller which monitors the region of the sample being scanned and scan position. The comparison signal enables position data from the controller to be stored in a position memory when the sample signal differs from the exemplar signal. As a result, the memory stores position data relating to potential defects, while data relating to positions where the sample matches the exemplar is simply discarded. In addition to position data, phase data reflected in the duration and direction of differences between the sample and exemplar signals can be stored along with respective position data to help characterize certain types of deffects.

The main advantage of the invention is that it provides data directly relating to differences in form between the sample and the exemplar. Where reflectivity data might indicate the presence or absence of a feature, e.g., a gold contact or a dioxide wall, the form data can indicate when an intended feature, while there, deviates from the proper thickness or height relative to nearby features. Thus, the present invention provides a more subtle analysis of quality inspection information than is available from systems which only generate reflectivity data alone.

The phase data provided by the present invention identifies regions where the defect is in the form of a misalignment of a feature or a thicknes offset. Such defects can be recognized when several nearby defects correlate with similar phases. Recognition of defect type is critical for development purposes-it provides insight into the source of the defects and, thus, aids in their correction. This type of data is difficult to obtain using CCD imaging.

The comparison of interferometric images can be very fast; it is limited basically by the speed at which the sample can be optically scanned. In general, the slit used for scanning is elongated so that several or many pixels can be scanned concurrently. The process is not slowly by the need to store and retrieve an image, whether using holographic film or a CCD. The comparison proceeds synchronously with the scan and the desired defect position data is stored with negligible delay. In addition, loss of resolution due to image storage and retrieval is avoided by the present invention. On the other hand, the present invention is flexible in its use of real and virtual exemplars.

The resulting defect location data is digital and concisely represented. Basically, the position memory accumulates a simple list of defect locations along with pertinent phase data. The data represents differences in form, with reflectively data largely filtered out.

Resolution is improved. The sample image scanner uses a slit to scan the sample interferometric image. Thus resolution is diffraction limited, typically to about 10 microns. This higher resolution implies less image area requiring analysis. A one hundred times area magnification is required to resolve 1 micron features, as opposed to the six hundred twenty-five times area magnification required for CCD imagers. This resolution advantage is basically a speed advantage in that one-/sixth the area after magnification need be analyzed.

Thus, the present invention flexibly provides more useful information more quickly and in a concise and convenient format. These and other features and advantages of the present invention are apparent from the description below with reference to the following drawings.

In the figures, a component, element or step referenced by a three digit number has as its first digit the figure number in which it was introduced. For example, sample imager 111 is first shown in FIG. 1 and sample 201 is first shown in FIG. 2. This is intended to aid the reader locate a referent when it is not shown in the figure to which a given portion of the following description is explicity referring.

DESCRIPTION OF THE PREFERRED EMBODIMENTS

Figure 1:
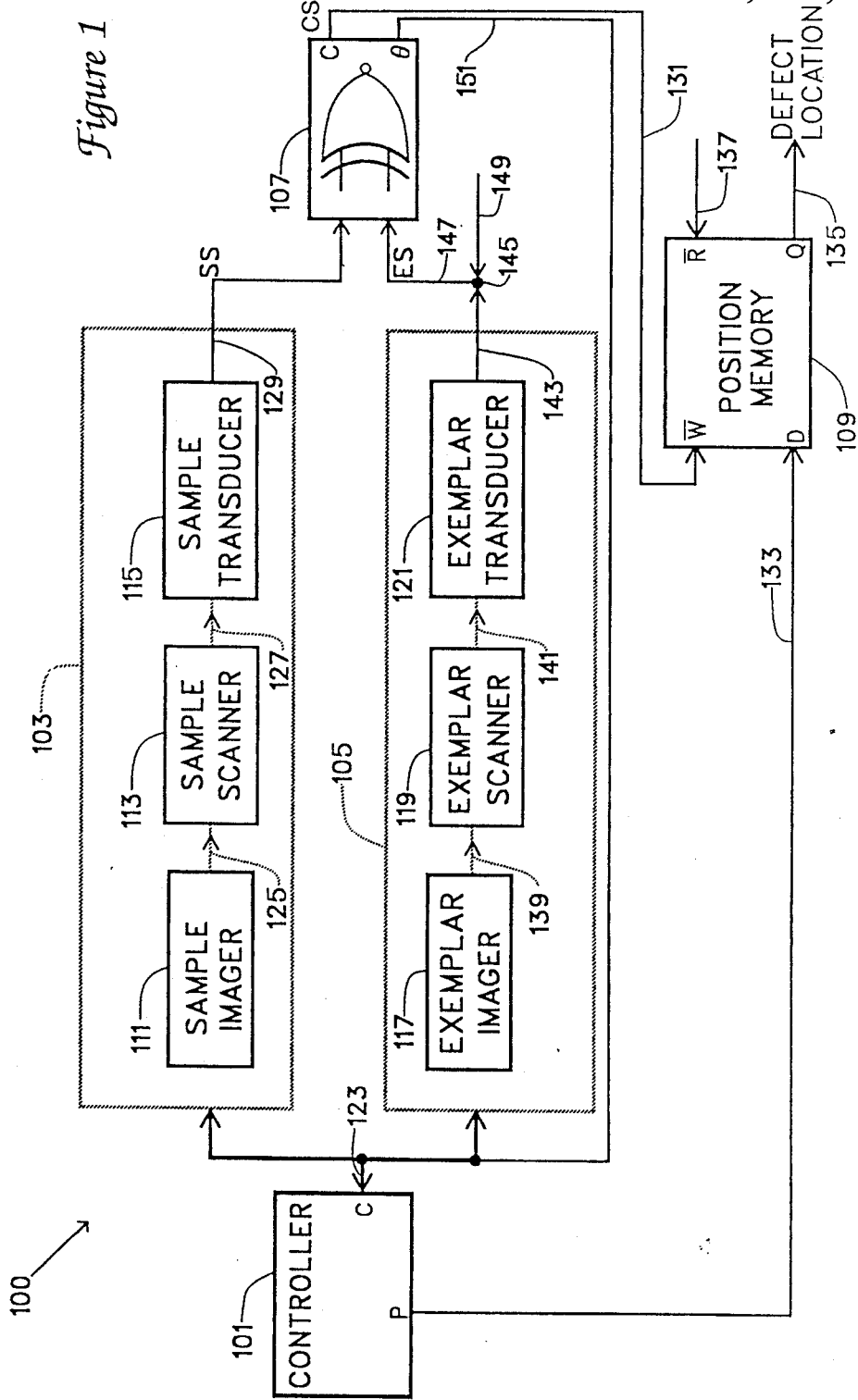
FIG. 1 is a schematic diagram of a quality inspection system in accordance with the present invention.

In accordance with the present invention, a quality inspection system 100 comprises a controller 101, a sample analyzer 103, an exemplar analyzer 105, a comparator 107, and a position memory 109, as shown in FIG. 1. Sample analyzer 103 includes a sample imager 111, a sample scanner 113, and a sample transducer 115; likewise, exemplar analyzer 105 includes an exemplar imager 117, an exemplar scanner 119, and an exemplar transducer 121.

Figure 2:
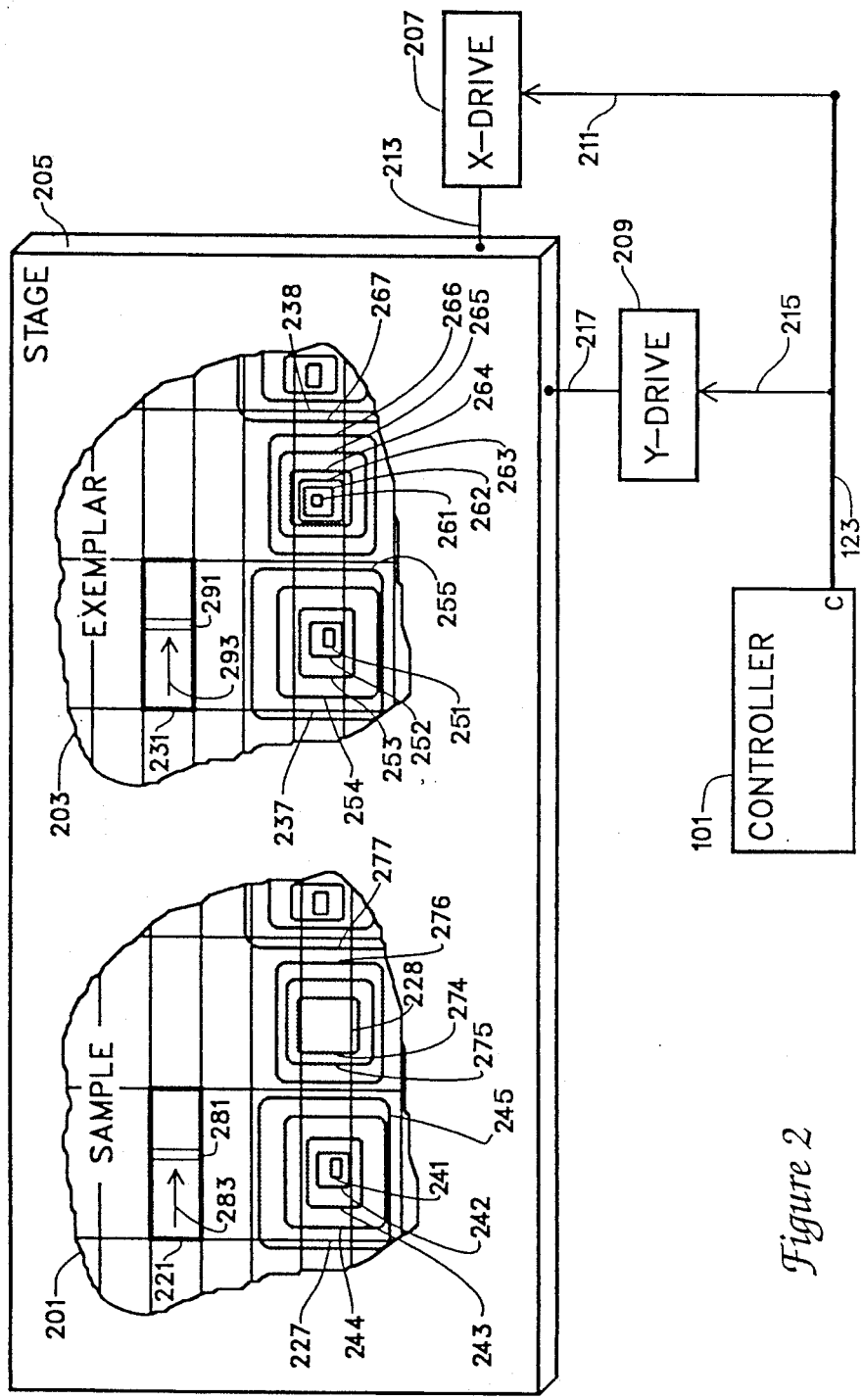
FIG. 2 is a schematic view of a sample to be compared with an exemplar in the quality inspection system of FIG. 1.

The purpose of quality inspection system 100 is to provide for a rapid and concise comparison of the three-dimensional forms of a sample 201 and an exemplar 203, schematically shown in FIG. 2. Exemplar 203 is an exemplary wafer at some stage of integrated circuit processing; sample 201 is a wafer at the same stage of processing whose quality is to be determined. Potential defects are indicated wherever sample 201 differs from exemplar 203.

Controller 101 is coupled to analyzers 103 and 105 via a control bus 123 for coordinating the actions of the analyzers' components, as shown in FIG. 1. The individual lines of bus 123 are described below. Sample imager 111 provides an interferometric image which is transmitted via beam path 125 to sample scanner 127, which scans the sample image to yield a sample scan in the form of a time-varying intensity. The sample scan is transmitted via beam path 127 to sample transducer 115 which converts it to an electrical signal SS in which signal level corresponds to scan intensity. For signal SS, voltage varies with time just as intensity varies with spatial position in the interferometric image of sample 201. Signal SS is transmitted via line 129 to comparator 107.

Comparator 107 compares sample signal SS with an exemplar signal ES, in effect, providing an exclusive-nor (XNOR) logical combination of the signals. In other words, the comparaison signal CS output form comparator 107 is high when SS and ES are the same and low when they are different. Comparison signal CS is transmitted via line 131 to the write enable input of position memory 109. When activated by a logic low (when SS is different than ES), position memory 109 stores position data received at its data port via line 133 from the position data output P of controller 101. A host system can read the stored position data along line 135 from the output of position memory 109 by enabling its read enable port via 137. These operations are performed in conjunction with convention addressing, the ports and lines for which are implied in FIG. 1.

Exemplar signal ES can be generated concurrently with sample signal SS. An exemplar image is transmitted from exemplar imager 117 via beam path 139 to exemplar scanner 119. Exemplar scanner 119 transmits the scanned exemplar image along beam path 141 to exemplar transducer 121. Exemplar transducer 121 converts the resulting exemplar scan into exemplar signal ES and transmits this signal via lines 143, node 145, and line 147 to comparator 107.

Comparator 107 can also receive an exemplar signal along line 149 from a host computer. In this case, exemplar signal ES does not result from concurrent imaging and scanning of an exemplar along with a sample. The exemplar signal can result from a retrieval of a previously stored exemplar signal, previously generated using interferometric imaging and scanning or it can be a simulated exemplar signal generated from a computer model for the design of the sample. Thus the present invention provides for flexibilty in selection of exemplar signal sources.

Since it can be impracticable to cover an entire wafer in a single scan, quality inpection system 100 is designed to scan a sample region-by-region. Controller 101 controls the X-axis and Y-axis movement of a translation stage 205 via an X-drive 207 and a Y-drive 209 to select a region to be analyzed. X-drive 207 is coupled to control bus 123 via a line 211 and is mechanically coupled to stage 205 via a link 213; Y-drive 207 is coupled to control bus via a line 215 and is mechanically coupled to stage 205 via a link 217. Since sample 201 and exemplar 203 are both positioned on stage 205, their initial alignment is maintained throughout the process of locating defects.

The step-wise motion of stage 205 defines regions of sample 201, including regions 221, 227 and 228. The same motion also defines regions of exemplar 203, including regions 231, 237 and 238. For example sample region 227 and exemplar region 237 are analyzed simultaneously. With sample 201 and exemplar 203 properly aligned, exemplar region 237 includes features which, in the absence of defects, should be duplicated in sample region 227.

Quality inspection system 100 compares interferometric images rather than pixel-based images. The appearance of sample 201 and exemplar 203 to their respective imagers 113 and 119 are indicated for sample regions 227 and 228 and exemplar regions 237 and 238. For example, sample region 227 provides a generally rectangular curve corresponding to a peak 241 of a local feature. Curves 242, 243 and 244 indicated successively lower contour lines corresponding to the same feature. An essentially identical feature is located in exemplar region 237, hence the correspondence of curves 251-254 with lines 241-244.

Sample region 228 differs from corresponding exemplar region 238. Specifically, sample region 228 does not include curves corresponding to curves 261-263 of exemplar region 238. These curves correspond to the highest points on a local feature which also defines curves 264-267 in exemplar region 228. This type of discrepancy indicates that the top of the corresponding feature on sample 201 either failed to form or was destroyed so that sample region 228 only includes curves 274-277 corresponding to curves 264-267 of exemplar region 238.

A major function of quality inspection system 100 is to signal the difference between sample region 228 and exemplar region 238 while they are being scanned so as to indicate the location of the difference and presumed defect of sample 201. Since controller 101 determines the region being scanned, the region of a detected difference is known a priori. The position within a region is determined by the scan position of sample scanner 113.

Sample scanner 113 effectively scans a transversely elongated slit longitudinaly across the region being scanned. The area viewed by the slit at one instant during a scan is indicated schematically by rectangle 281 in sample region 221, while the direction of scan is indicated by longitudinal arrow 283. Rectangle 291 indicates the area scanned by exemplar scanner 121 at the same instant, while arrow 293 indicates the direction of scan for exemplar region 231. Controller 101 determines the position of each slit at each instant during a scan. When a difference is detected, the current slit position is used to determine a defect's longitudinal position within a sample region.

Figure 3:
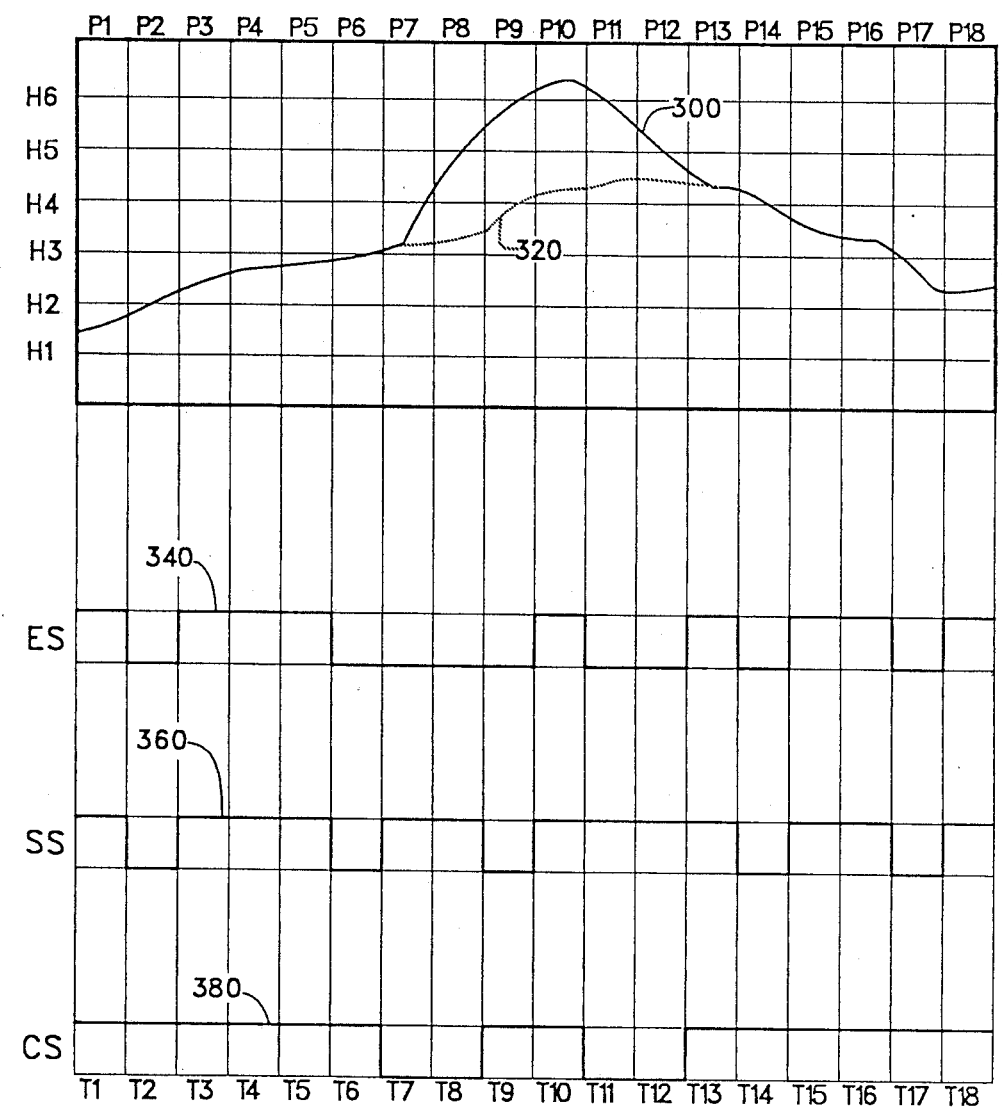
FIG. 3 is a graph of height profiles for the sample and exemplar of FIG. 2 along with corresponding signal forms.

FIG. 3 depicts height versus longitudinal position profiles for corresponding sample and exemplar regions, such as regions 228 and 238. Profile 300 is a profile of an exemplar region, and profile 320 is a profile of a corresponding sample region. Profile 320 is shown as a broken line where it deviates from profile 300; elsewhere, the profiles are superimposed. Profiles 300 and 320 are plotted over a range of heights (H1-H6) versus longitudinal positions P1-P17. Each unit height represents the height resolvable by the interferometric imager employed, e.g., sample imager 111 or exemplar imager 117, and is a function of the wavelength employed in obtaining an interferometric image. Each unit of position corresponds to the longitudinal extent at the region being scanned corresponding to the width of the slit used in scanning. Height is not resolved along the length of a slit, so each height is an integration over the transverse extent of a region. Of course, at the cost of scanning speed, the slit can be made shorter. In the limit imposed by diffraction, the "slit" can be one-half wavelength square, e.g., about 10 microns on a side.

Exemplar analyzer 105 yieds a exemplar signal ES which appears as signal 340 when profile 300 is scanned. Signal 340, which is idealized for expository purposes, is high except when a cancellation curve, such as curve 265, is being scanned, in which case, signal 340 goes low. A cancellation curve occurs at positions in which a profile crosses a unit height interval. For example, during T1, P1 is scanned and profile 300 remains between H1 and H2 so no cancellation curve is encountered and signal 340 remains high. During T2, P2 is scanned and profile 300 crosses H2; a cancellation curve is encountered and signal 340 goes low.

Sample analyzer 103 yields a sample signal SS which appears as signal 360 when profile 320 is scanned. Signal SS is generated in the same manner as signal ES. Therefore, signals 340 and 360 are identical during times corresponding to positions over which profiles 300 and 320 are identical. Profiles 300 and 320 are identical for positions P1-P6 and P14-P18; consequently, signals 340 and 360 match for time intervals T1-T6 and T14-T18. Deviations between signals SS and ES indicate differences in the profiles scanned; for example, profiles 300 and 320 are different over positions P7-P13, and this difference is reflected in differences between signals 340 and 360 during time intervals T7-T13.

Comparator 107 functions as an X-NOR gate, yielding a signal CS from the combination of ES and SS. Accordingly, signal 380 is generated from signals 340 and 360. Signal 380 is low during time intervals T7, T8, T11 and T12, accordingly, positions P7, P8, P11 and P12, and the X, Y coordinates for the region being scanned are transmitted. The position data generated fairly characterizes the differences in between profiles 300 and 320, which extend from P6-P13. In general, sample signal SS is generally not synchronous with exemplar signal ES so comparison signal can include pulses with fractional durations, the fractions corresponding to phase differences between the sample and exemplar interference patterns. This phase information can be used to allow a measure of the degree of discrepancy between sample and exemplar. Accordingly, a replica of CS can be inverted, integrated, digitized and fed back to controller 101.

Digitized phase information is provided by comparator 107 at its $\theta$ output and transmitted to controller 101 via line 151 and bus 123. Controller 101 can then pass this phase information along with position information to position memory 109. When a host computer accesses memory 109, it can acquire the phase information relating to a defect as well as its position.

In the event that several nearby defect positions have similar associated phases, this indicates a regional defect rather than a highly localized defect. For example, in comparing interferometric sample and exemplar images, it could be that the same fringe patterns are there, but one pattern is slightly displaced with respect to the other. This could happen due to a misalignment of part of an integrated circuit pattern or due to a difference in the thickness of the region to which the defect position data relates. The phase data can help distinguish such defects from strictly local defects and provide important guidance in improving the manufacturing process.

Figure 4:
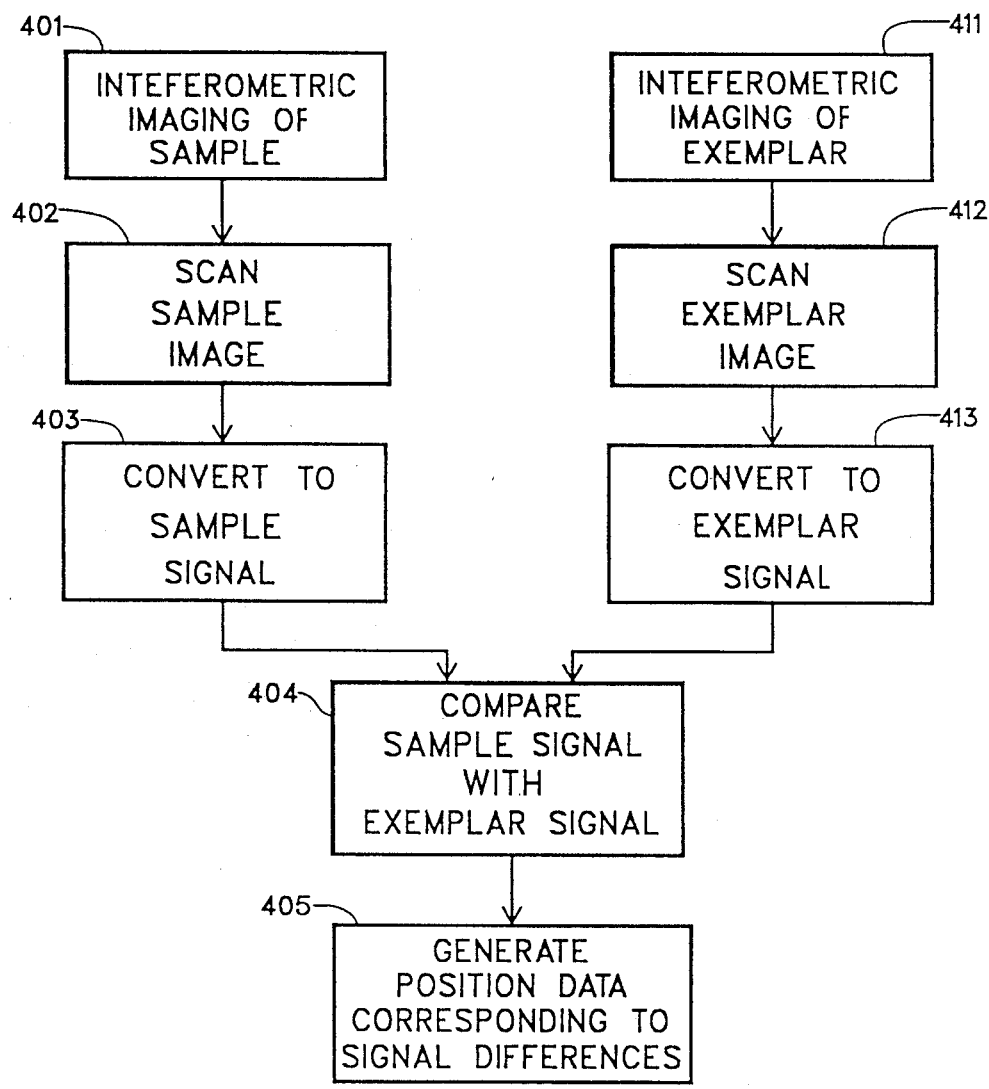
FIG. 4 is a flow chart of the method of the present invention.

The method of the present invention is depicted in the flow chart of FIG. 4. At step 401, an interferometric image of sample 201 is obtained, yieling a interferometric image as shown with respect to region 228. At step 402, this interferometric image is scanned by sample scanner 111. Scanning effectively converts position to time and the interferometric curves to a time-varying intensity. At step 403, the time-varying intensity is converted by sample transducer 117 to sample signal SS as represented by signal 360. At step 404, signal SS is compared with exemplar signal ES, as represented by signal 340, yielding comparison signal CS, represented by signal 380. At step 405, comparison signal CS is used to trigger the generation of position data used to indicate the location of deviations in a sample profile from an exemplary profile and thus indicate the location of sample defects. Note that while the method is described as a series of steps, the steps are sequential only on a quantum scale, i.e., as experienced by photons and electrons. Operationally, all steps are executed concurrently.

Exemplar signal ES can be generated by analyzing an exemplar synchronously with a sample. Thus, step 411 involves interferometric imaging of exemplar 203 concurrently with step 401. Exemplar 203 is scanned in step 412 synchronously with the scanning of sample 201 in step 402. Exemplar signal ES is provided in step 413, just as sample signal SS is provided in step 403.

Figure 5:
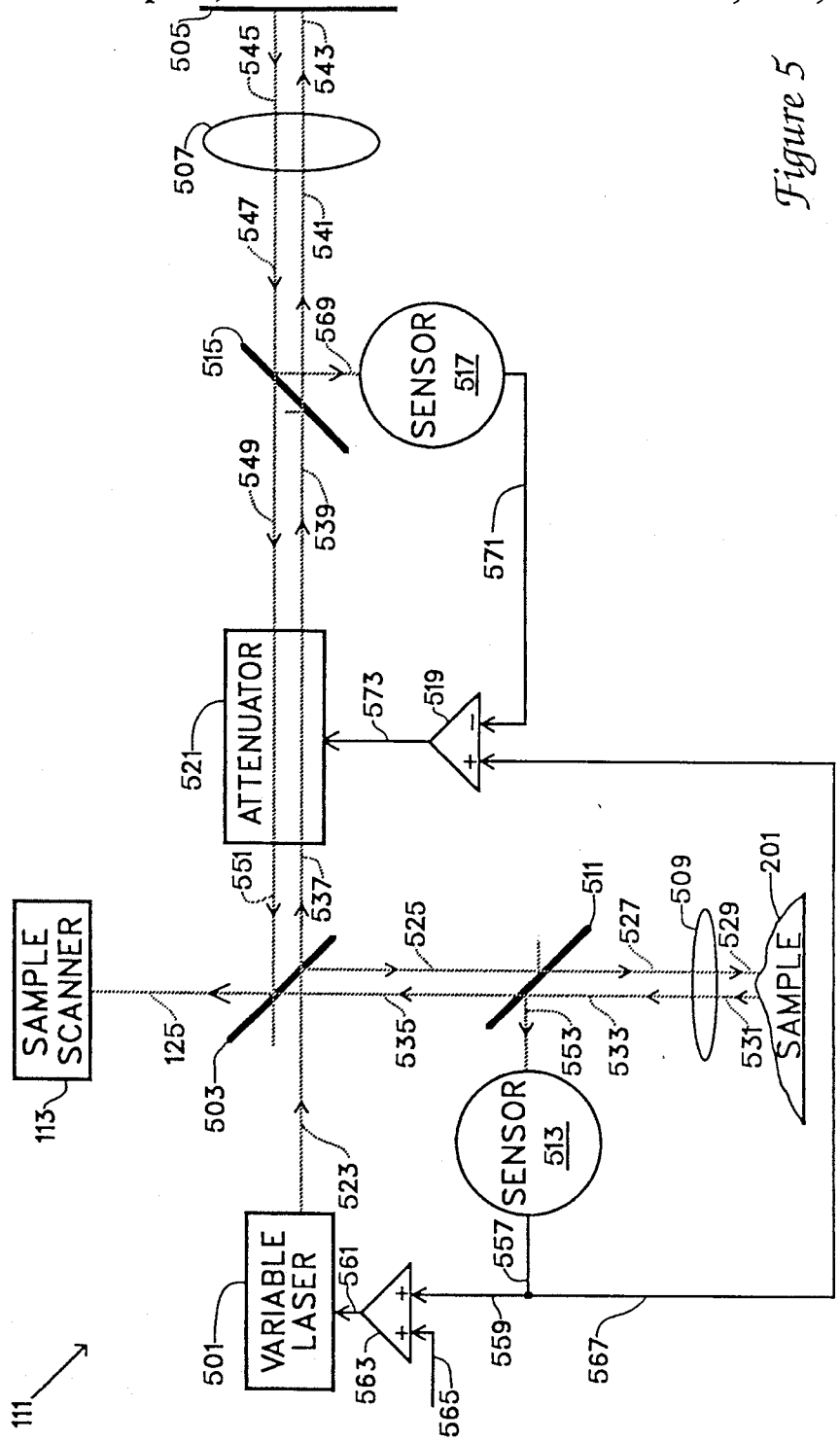
FIG. 5 is a schematic diagram of the sample imager of FIG. 1.

Sample imager 111 is shown in greater detail in FIG. 5; exemplar imager 117 is essentially equivalent and so is not described separately. Sample imager 111 comprises a variable intensity laser 501, a main beam-splitting mirror 503, a reference plane 505, a reference objective lens 507 and a sample objective lens 509 arranged in a conventional interferometric configuration. Additional components including a sample beam-splitting mirror 511, a sample sensor 513, a reference beam-splitting mirror 515, a reference sensor 517, a differential amplifier 519 and an attenuator 521 are used to compensate for differences in reflectively between sample regions.

The output of variable laser 501 traverses beam path 523 to main beam-splitting mirror 503. The "sample" laser component reflected thereby is transmitted along beam path 525 and most of it passes through sample beam-splitting mirror 511 to beam path 527. This sample laser component is focused by sample objective lens 509 along beam path 529 onto sample 201. Sample 201 reflects the incident beam, introducing phase distortions as a function of the sample profile. The phase distorted beam is transmitted along beam path 531, through objective lens 509 and along beam path 533 to sample beam-splitting mirror 511. Most of the light reflected from sample 201 is transmitted through sample beam-splitting mirror 511 and along beam path 535. Half of the light along beam path 535 contributes to the interference pattern output along beam path 125 to sample scanner 113, the remaining half necessarily being diverted toward laser 501.

The "reference" laser component transmitted through main beam-splitting mirror 503 is transmitted along beam path 537, mostly through attenuator 521, along beam path 539, mostly through reference beam-splitting mirror 515, along beam path 541, through reference objective lens 507, and along beam path 543 to reference plane 505. The incident light is reflected, ideally without phase distortions, back along beam path 545, through reference objective lens 507, along beam path 547, mostly through reference beam-splitting mirror 515, along beam path 549, mostly through attenuator 521 and along beam path 551 to main beam-splitting mirror 503. Half of this reference beam is reflected by main beam-splitting mirror 503 and this half interferes with the sample component from beam path 535 to produce fringe patterns along beam path 125, such as those shown superimposed on regions 227 and 228 in FIG. 2.

A fraction of the light reflected by sample 201 and transmitted along beam path 533 is diverted by sample beam-splitting mirror 511 along beam path 553 to sample sensor 513 to provide a measure of the overall reflectivity of the sample region being scanned. Sample sensor 513 thus provides a control signal, along line 557 and branch 559, through a summing amplifier 563, and along line 561 to variable laser 501. This control signal is used to control the intensity of the output of variable laser 501 to compensate for differences in reflectivity across sample regions.

Without additional compensation, the contribution of the reference beam along beam path 551 to the interferometric image along beam path 125 changes with the output intensity of variable laser 501. Since laser output intensity is varied to provide for a relatively constant intensity for the sample component of the interferometric image it is desirable to maintain a substantially constant intensity for the reference component as well. To maintain a reference beam of substantially constant intensity the reference beam must be variably attenuated to compensate varying laser output. Branch 567 from line 557 carries the sample sensor output to the "+" input of differential amplifier 519. In addition, reference beam-splitting mirror 515 diverts a fraction of the reference beam along beam path 547 to reference sensor 517 via beam path 569. The output of reference sensor 517 is directed along line 571 to the "−" input of differential amplifier 519. The output of differential amplifier 519 is directed along line 573 to attenuator 521 which is regulated to compensate for changes in laser intensity. More specifically, the arrangement including differential amplifier 519 forces the overall intensity of the reference beam along beam path 551 to track the overall intensity of the sample beam along beam path 535. In this way, the intensities of the components of the interference are balanced within an optimal intensity range, which condition provides the most distinct interference pattern to sample scanner 113.

Figure 6:
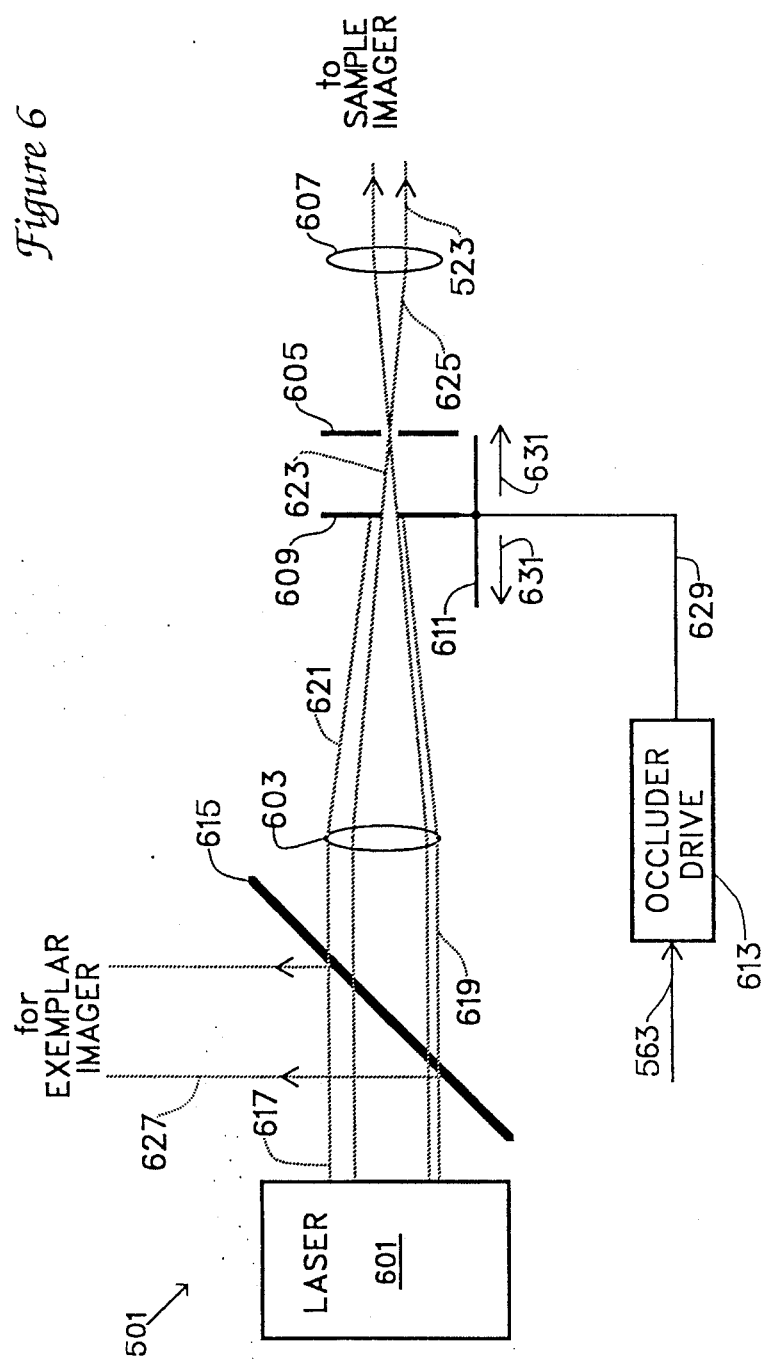
FIG. 6 is a schematic diagram of the variable laser of FIG. 5.

Variable intensity lasers are typically configured with a pair of polarizers which can be rotated relative to each other to attenuate laser output. Instead, variable laser 501 uses an occluding pinhole, as described with reference to FIG. 6. Variable laser 501 comprises conventional components including a laser 601, a converging lens 603, a pin-hole spatial filter 605, and a collimating lens 607. A pin-hole occluder 609 is mounted on a base 611 which can be moved between converging lens 603 and spatial filter 605 when an occluder drive 613 is actuated. In addition, laser 501 employs a system beam-splitting mirror 615 so that it can be used by exemplar imager 117 as well as sample imager 111.

The output of laser 601 is transmitted along beam path 617. The component of the laser output transmitted through system beam-splitting mirror 615 is transmitted along beam path 619 to converging lens 603. The laser beam along beam path 621 converges toward the pin-hole of spatial filter 605. However, to an extent depending on its longitudinal position, occluder 609 blocks a portion of the light along beam path 621 and transmits the remaining portion along beam path 623 to spatial filter 605. The light diverges along beam path 625 and is collimated by collimating lens 607 to provide the output of variable laser 501 along beam path 523.

The longitudinal position of occluder 609 between converging lens 603 and spatial filter 605 is controlled by the output of sample sensor 513 along branch 563, which actuates occluder drive 613. Occluder drive 613 is mechanically linked to occluder base 611 via link 629. Arrows 631 indicate the directions of motion available to occluder 609. Movement toward converging lens 603 decreases laser output intensity while movement toward spatial filter 605 increases laser output intensity. The component of the output of laser 601 reflected along beam path 627 by system beam-splitting mirror 615 is used for exemplar imager 117 in the same manner as the component transmitted therethrough is used for sample imager 111.

Figure 7:
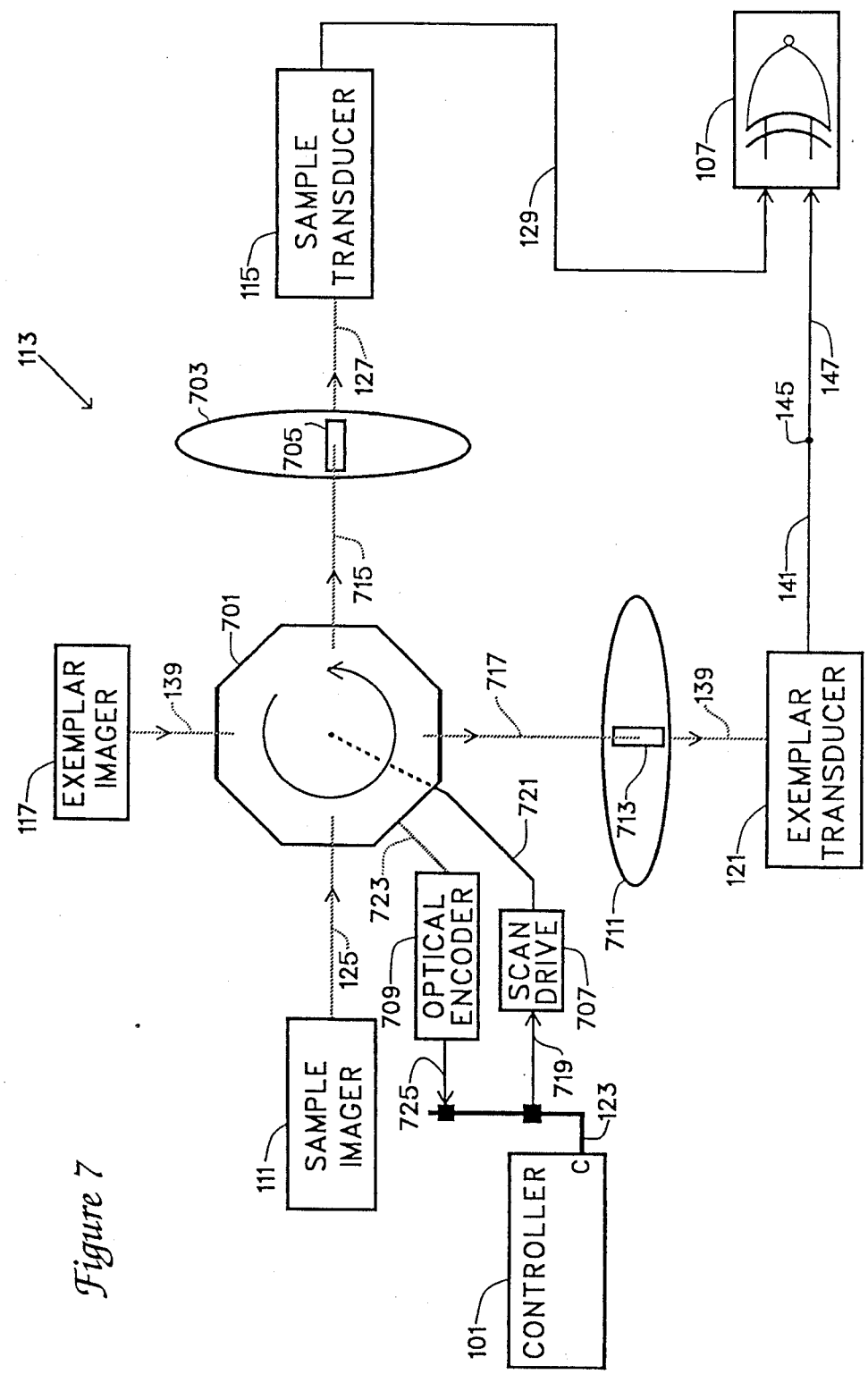
FIG. 7 is a schematic diagram of the sample and exemplar image scanners of FIG. 1.

Sample scanner 113 comprises a scaning prism 701 and a frame 703 for a slit 705, as shown in FIG. 7. Controller 101 controls the motion of scanning prism 701 using a scan drive 707. The scan position of scanning prism 701 is monitored using an optical encoder 709. Scanning prism 701, scan drive 707 and optical encoder 709 are shared by exemplar scanner 119. In addition, exemplar scanner 119 includes a frame 711 for a slit 713. Since sample scanner 113 and exemplar scanner 119 share scanning prism 701, synchronization of the sample and exemplar scans and thus of sample signal SS and exemplar signal ES is straightforward.

An image, such as that represented in sample region 228 of FIG. 2, is transmitted from sample imager 111 along beam path 125 to scanning prism 701. Scanning prism 701 refracts incident light at an angle dependent on its instantaneous orientation, which is continually changing due to the action of scan drive 707, which is basically a DC motor. Thus, the portion of the beam transmitted along beam path 715 and incident slit 705 changes as scanning prism 701 rotates. As a result, the portion of the image transmitted along beam path 127 to sample transducer 115 is continually changing.

The portion of the sample image passed by slit 705 is represented in FIG. 2 by rectangle 281, which is the reverse projection of slit 705 onto sample region 221. Arrow 283 corresponds to the rotational direction of scanning prism 701. As a result of the scanning, the portion of the sample image transmitted along beam path 127 to sample transducer 115 sometimes includes a dark interference band and sometimes does not. When it does, sample signal ES is low, otherwise it is high. The transitions can be made sharp using a threshold device as explained below with reference to FIG. 8. As discussed above, the output of sample transducer 115 is directed along line 129 to comparator 107.

The exemplar image, which is represented by curves 261–267 for exemplar region 238 in FIG. 2, is processed concurrently and in a similar manner. The exemplar image is received from exemplar imager 117 along beam path 139 and variably refracted by scanning prism 701. The variably refracted image is transmitted along beam path 717 to slit 713. The reverse projection of slit 713 onto exemplar region 231 is shown by rectangle 291 in FIG. 2, while the rotational direction of scanning prism is represented by arrow 293. The scanned portion of the exemplar image is transmitted along beam path 141 to exemplar transducer 121. The output of exemplar transducer 121, which corresponds to exemplar signal 340 in FIG. 3, is transmitted along line 143 toward comparator 107.

Scan drive 707 and optical encoder 709 are controlled by controller 101 via control bus 123. Scan drive receives control signals, e.g., on and off, from control bus 123 via line 719 and mechanically executes the embodied commands via link 721. Optical encoder 709 detects the passage of strobe marks on a shaft of scanning prism 701 via beam path 723 to monitor its rotational position. The results are transmitted along line 725 and control bus 123 to controller 101 for use by position memory 109.

Figure 8:
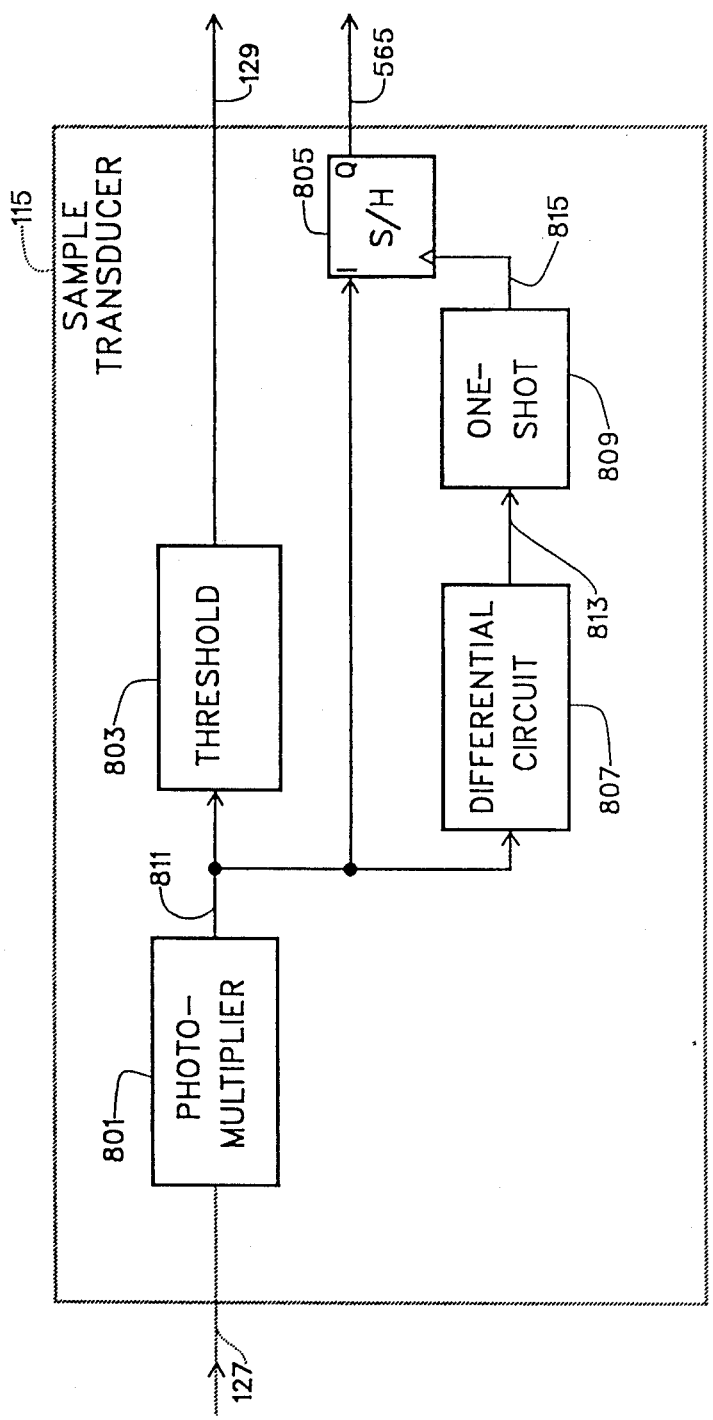
FIG. 8 is a schematic diagram of the sample transducer of FIG. 1.

Sample transducer 115 comprises a photo-multiplier 801, a threshold device 803, a sample-and-hold circuit 805, a differential circuit 807, and a one-shot 809, as shown in FIG. 8. The sample scan is received along beam path 127 by photo-multiplier 801. The sensitivity available in photo-multiplier's is typically around 10,000 times that available from CCDs; this is a reason for the superior performance of quality inspection system 100 relative to those based on CCD imaging. The signal output along line 811 varies in proportion to the intensity of the scanned input to photo-multiplier 801. Threshold device 803 is used to obtain a binary output such as those shown by sample signal 360 in FIG. 3. This binary output serves, via line 129, as the input enable to position memory 109.

The interferometric sample image is a superposition of an interferometric pattern on a reflectivity distribution corresponding to the region of the sample being scanned. When sample slit 705 is not viewing an interference fringe, the photo-multiplier output basically represents the reflectivity pattern. Accordingly, variable laser 601 can be adjusted to compensate for reflectivity at a spatial frequency corresponding to a couple of slit width using feedback based on the photo-multiplier output.

To this end, sample-and-hold circuit 805 is arranged to sample the photo-multiplier output during scan times when no fringe is being viewed by sample slit 705 and to hold sampled values during scan times when a fringe is viewed by slit 705. Differential circuit 807 and one-shot 809 provide the timing for the sample-and-hold operation. The photo-multiplier output can be roughly characterized as a constant signal with downwardly pointing trapezoidal pulses corresponding to the appearance of fringes in the slits field of view. Differential circuit 807 converts this waveform to a ground level signal followed by a narrow downward spike followed by another ground level signal, and then an upward spike. The upward spike is followed by another ground level signal corresponding to the next "interfringe" portion of the scan cycle.

The spike pattern is transmitted to one-shot 809 via line 813. One shot 809 responds only to upward spikes to which it responds with a clean pulse of a fixed duration about one half the minimum expected fringe separation in an interferometric image. The one-shot output is transmitted along line 815 to a clock input of sample-and-hold circuit 805. Sample-and-hold circuit 805 samples while the one-shot output is high and holds while it is low. This has the desired result of sampling when no fringes are being viewed and holding while fringes are being viewed. The sample-and-hold output is transmitted along line 565 which is an input to summing amplifier 563 which controls variable laser 501. In effect, the described feedback from sample transducer 115 provides high spatial frequency reflectivity filtering in addition to the low spatial frequency reflectivity filtering provided by the feedback from sample sensor 513. The two levels of reflectivity filtering maintain an optimal signal-to-noise ratio throughout quality inspection system 100.

Quality inspection system 100 is designed so that regions can be scanned in rapid succession. For this to happen, it is necessary that stage 205 be positioned with great precision, e.g., to within 1 $\mu$m, and with great speed. In other systems, precise positioning implies significant mechanical isolation from ambient shocks and vibrations. To the contrary, quality inspection system 100 uses ultrahigh speed, closed loop positioning to offset vibrations so that elaborate mechanical isolation devices need not be employed.

High speed positioning is provided in part by asynchronous operation of X-drive 207 and Y-drive 209.

Movement in each axis, e.g., X and Y, is directed independently of movement in the other. Thus, movement along each is optimized without concern for the specific path taken to reach a desired endpoint. Movement of stage 205 along each axis is monitored by a respective laser interferometer. Position feedback from each interferometer is compared with a programmed destination to set optimal speed during stage travel. For example, when feedback indicates that the stage is within a predetermined range of the destination for the respective axis, the speed decays to provide a smooth stop at the desired point. Comparison of monitored position with destination is performed in real-time by dedicated circuitry so there is no need to wait for microprocessor intervention.

Actual positioning is provided using enhanced precision stepper motors. X-drive 207 and Y-drive 209 use identical stepper motors, so only the motor for X-drive 207 is described in detail. This stepper motor is conventional except as to the signal used for driving it. The stepper motor includes a threaded shaft which is rotated by a changing magnetic field. The precision of the stepper motor is determined in part by the pitch of the thread: a finer pitch permits more precise positioning. However, there are material/mechanical limits to how fine a pitch can be used. X-drive 207 uses a uniquely driven stepper motor to provide greater positioning precision for any given pitch of the shaft threads.

The stepper motor includes multiple coils, each dedicated to driving a respective "phase" of the motor. Typically, the coils are driven in alternation by binary signals. The binary signals are out-of-phase with respect to each other so that the coils activate magnetic fields in turn, urging a rotor and the attached shaft to turn.

The stepper motor used in X-drive 207 is not driven by bi-level signals, but rather by multi-level signals. The multi-level signals are generated by repeated sampling and holding of a rectified cosine wave. The result is a step-wise approximation of the rectified cosine wave. The drive signals are staggered with respect to each other. Since the present stepper motor uses two coils, the drive signals are generated out-of-phase so that one reaches its maximum while the other is at its minimum. The corresponding coils are arranged orthogonal to each other, as in a convention stepper motor. The effect of the stepped cosine signals is that, instead of acting in alternation, they add vectorially, tracing a circle over time. While a conventional stepper motor might have four discrete rotational positions per revolution, the present stepper motor has as many as there are sample-and-hold steps over half a cosine cycle. Thus, the precision of a conventional stepper motor is significantly enhanced.

The present invention provides for modifications, variations and extensions to quality inspection system 100 as described above. Provisions are made for alignment of fringes, variations on scanning, reflectivity filtering, and signal processing. Furthermore, provisions are made for taking metrologies about locations identified for possible defects.

The signal-to-noise ratio for sample signal SS is greatest when fringes are aligned with slit 705. When fringes are not aligned with the slit, the slit views several fringes and intermediate spaces at once, rather than in sequence. The bright spaces and dark fringes are integrated over the slit, yielding an intermediate signal which is difficult to interpret.

In a typical integrated circuit, most of the features extend along either one of two orthogonal axes. Therefore, it is usually feasible to align a sample integrated circuit so that roughly half of the interference fringes are aligned with slit 705. A lesser precentage is attainable for samples with irregular features.

Discrepancies in fringes not aligned with slit 705 are difficult to detect. This raises the questions as to whether defects are being missed by the scanning method describe above. The answer, for the most part, is no. Generally, a defect causes discrepancies in fringes extending in several different directions. While discrepancies in fringes not aligned with a slit may not be detected, the defects causing those discrepancies can be detected by discrepancies in other fringes that are aligned with a slit. Thus, while some of the data reflected in a defect is missed, the defect itself is located.

Nonetheless, the chances of detecting defects can be enhanced by adjusting the alignment of fringes with a slit by rotating the incorporating interferometric image relative to the slit. The information used for alignment can be encoded with position data to characterize the local slope of the fringes. This relative rotation can be provided by rotating sample frame 703 and thus slit 705 relative to a stationary sample image. Similarly, exemplar slit 713 can be rotated relative to the exemplar image. Frame 703 can be marked so that its rotational position can be monitored by an optical encoder. When sample slit 705 and exemplar 713 are aligned differently, the difference can be calculated and stored as defect data.

It is also possible to move the image relative to a stationary slit, for example using a dove prism. A dove prism is an optical device which, when rotated through an angle, can rotate an image through twice that angle. Thus, alignment can be effected by rotating a dove prism configured along the image path.

The effect of the dove prism depends on its position along the beam path relative to scanning prism 701. A dove prism between scanning prims 701 and slit 703 rotates the sample image after it is swept; the scan direction (arrow 283) relative to the region being scanned is unchanged, but the angle of the back-projection (rectangle 281) of the slit onto the region is changed.

If scanning prism 701 is between the dove prism and slit 705, then the image is rotated before it is swept; this changes the direction of the scan relative to the sample. In other words, arrow 283 in sample region 221 becomes tilted relative to its positions as shown in FIG. 2. In effect, back-projection rectangle 281 is rotated with scan direction arrow 283 so that slit 705 extends orthogonal to the scan direction. Therefore, the region scanned is orientated obliquely relative to sample regions 221, 217 and 218 of FIG. 2.

To achieve the desired alignment, whether by rotating a slit or a dove prism, actual alignment must be detected. This can be done using a quad detector, which is a device with four photo-electric quadrants, which can be labeled A, B, C and D going clockwise about the center of the device. The quad detector can be aligned so that the boundary between quadrants B and C and between quadrants D and A is aligned with slit 705. (More specifically, a fringe aligned with this boundary is also aligned with slit 705.) The outputs of the quadrants can be coupled to differential amplifiers to provide an output $E = (A - D) - (B - C)$. This output E is zero when the fringe or fringes incident to the quad detector are properly aligned. Otherwise, output E is not zero and can be used as a control signal to effect a relative rotation until the desired alignment is achieved. A corresponding configuration can be used for exemplar slit 713.

The quad detector can be selected to correspond to the area viewed by slit 705 or to correspond to a larger area, such as region 221. The advantage of a larger area is that the scan direction and slit alignment can be optimized for a given region and then maintained during the scan. However, more precise alignment on a fringe-by-fringe basis requires that the quad detector area correspond to the slit area. In this case, the quad detector should be arranged to receive a portion of the interferometric image after it is swept by scanning prism 701. The quad detector can be mounted on frame 703, which has the advantage that it rotates with slit 705. Otherwise, the quad detector can be mounted in some other rigid relation relative to slit 705.

The quad detector can intercept the same sweep received by the slit. For example, the quad detector can be placed to anticipate the slit's view. Alternatively, a beam-splitting mirror can be used to generate a parallel image, which is also swept by scanning prism 701 so that the quad detector and slit 705 view the same portions of the interferometric image at the same time.

If the quad detector is selected to view the entire region being scanned, a beam-splitting mirror can be used to divert a portion of the image beam along beam path 125 before it is swept. This diverted portion is directed to the quad detector. This approach is useful for detecting defects in which an entire region of an integrated circuit may be misaligned relative to the rest of the integrated circuit. In this event, the sample image will be aligned differently than the exemplar image. The difference in the sample and comparison alignment signals can then be used as an alternate enable signal for the position memory.

Feedback from the quad detector, or other orientation sensor, can be used in several ways. It can be used to rotate: a slit; a dove prism placed before or after the scanning prism, or stage 205 to a desired orientation. It can be used to select among several slits at different fixed orientations as the source for the scan. In this case, each slit can have its own photo-multiplier. In addition, the multiple slit approach can employ means for comparing the outputs of several slits at once and selecting the slit output with the strongest fringe definition. Slit selection can be monitored to provide orientation information on the fringes. Another approach to handling fringes at different angles is to perform multiple scans.

In the illustrated embodiments, reflectivity filtering is performed using light reflected from a sample region and also using the sample signal level to regulate laser output. The light reflected from the sample region provides reflectivity filtering on a region-by-region basis. By using a CCD sensor as sample sensor 513, one can obtain the information required for pixel-by-pixel reflectivity filtering prior to scanning. The CCD can be "read-out" synchronously with the scan process to provide the desired filtering.

Instead of attenuating the overall laser output, one can use a pixel-based attenuator, i.e., one in which the spatial distribution of attenuation can be controlled. The output of the CCD sensor can be used to control the spatial distribution of attenuation to complement the spatial distribution of reflectivity of the sample.

An attenuator can be placed in the sample arm of the interferometer, e.g., in beam paths 525 and 535. In this case, only a single attenuator is required, obviating the need for attenuator 521 to compensate intensity variations in laser 501 (which would be held at constant intensity). The attenuator in the sample arm could be uniform or pixel-by-pixel. These approaches to separating form from reflectivity can be replaced or complemented by mathematical deconvolution of the interferometric image.

In sample analyzer 103, an interferometric image is created and then scanned. Alternatively, the laser itself can be scanned over a sample region, much as a laser in a laser printer is scanned over the drum. In this case, there is never a complete interferometric image of a sample region. The scan is produced directly from the sample so it is not necessary that imaging and scanning be performed by separate components.

The scan converts the spatial distribution of intensity of the interferometric sample image to a temporal distribution of intensity. In other words, the scan is an optical signal which characterizes the interferometric sample image. Current technology favors processing electrical signals, so transducer 115 is provided to convert the optical signal to an electrical signal. However, the present invention provides for direct optical comparison of sample and exemplar scans to generate an optical comparison signal. In this case, the optical comparison signal can be further optically processed or converted to electrical form for electrical signal processing.

An alternative method of producing a comparison signal CS is to arrange sample 201 and exemplar 203 in a single interferometer arrangement. In other words, exemplar 203 can be positioned in place of reference plane 505 in sample imager 111. The resulting interference pattern shows the differences between the sample and the exemplar. This interference pattern can be scanned and converted to an electrical signal to provide the comparison signal. This has the advantage of requiring only one interferometer. The disadvantage is that it does not permit recorded and simulated exemplar signals to be compared with the sample signal.

Sample transducer 115 includes a threshold device 803 so that it provides a binary sample signal SS at its output 129. Alternatively, this device can be omitted in the transducer so that SS and correspondingly exemplar signal ES are analog. The advantage of this approach is that SS, ES and an resulting unthresholded CS can more sensitively reflect their referents. The amplitude of differences and the timing of transitions can both be used to indicate the nature of detected discrepancies. A threshold device can be applied to a replica of the comparison signal CS to provide binary control for position memory 109.

The method of the present invention, as described above with reference to FIG. 4, yields a list of positions of potential defects. This list can be used to guide further analysis of sample 201. Specifically, one might wish to characterize precisely the form of an area about a defect location, i.e., obtain a metrology of the defect location. Such a metrology can be used using quality inspection 100 or a modification thereof. The basic idea is to use an interferometric image of a sample rather than a normal sample image, since the former provides form data in a purer form.

The main advantages of the interferometric images are that they represent three-dimensional form and that they represent it simply. The relative simplicity of an interferometric image compared to a normal image allows it to be described in a very compact format, which, in turn, saves storage space, communications bandwidth and processing time. For the purposes of a metrology, the information of interest is the two-dimensional shape of each fringe, its size, its location (relative to neighboring fringes), and its orientation (relative to neighboring fringes). Preferably, this is supplemented by relative height data.

The relative heights represented by the respective fringes in the interferometric sample-image can be distinguished by comparing it to a second interferometric sample image taken under a slightly different angle of illumination. The information provided by the second interferometric sample image can be encoded concisely into a representation or description of the first interferometric sample image. For example, each fringe in the first image can be assigned a height in half-wavelengths relative to an arbitrarily selected fringe or to a fringe whose absolute height is known a priori. Alternatively, both interferometric sample images can be maintained for later reconstruction or analysis. Another approach to resolving height sign ambiguity is to supplement interferometric analysis with a cruder analysis of a height profile. For example, one can use an objective lens with a shallow depth of field and move it relative to the sample and determine what parts move into focus and which move out of focus.

Even the crudest encoding of an interferometric image for a metrology can be a bit map, with one bit per pixel. No grey-scale information is required as would normally be used with a standard image. Since grey-scale is not required, there are several compacting algorithms that could effectively compress the bit map. Furthermore, the width of a fringe is not required. Therefore each fringe can be assigned, for example, a width of one pixel. A raster representation could be a series of numbers representing the number of pixels between interference fringes on each raster line of the interferometric image. Even more efficient compacting can be achieved by analyzing an interferometric into graphics primitives and coding the interferometric image accordingly as a computer-aided design data file, e.g., an Autocad file, a format defined by Autodesk, Inc., or a page description file, e.g., a Postscript file, a format defined by Adobe Systems, Inc. Such encoding is not only compact, but also flexible. They make it easy to compare images that are scaled, rotated or inverted relative to each other.

The encoding of an interferometric image can be performed using a stored complete image or can be based on a scan of an interferometric image. While using an image stored, by example, by a CCD, can introduced delays in obtaining a metrology, these delays are more acceptable than delays caused by image storage during initial inspection. This is because the initial inspection permit metrologies to be limited to relatively few and relatively small areas. The advantage of assembling a complete image is that there is more flexibility available to an encoding process in determining the most compact and useful description of an interferometric image.

Figure 9:
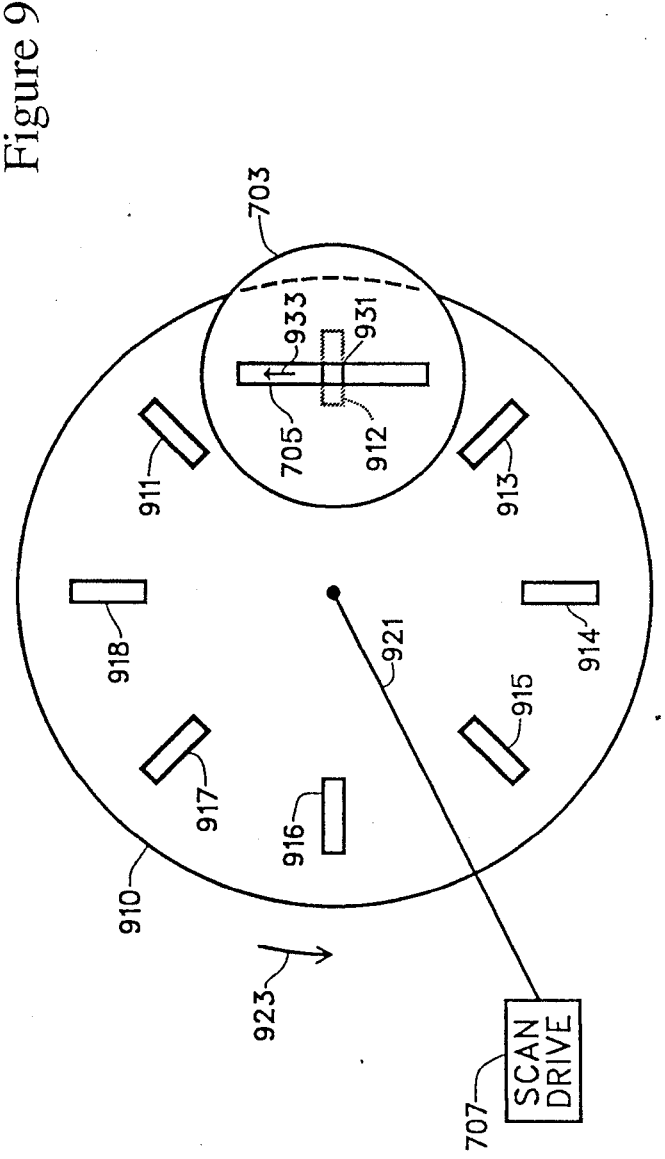
FIG. 9 is a schematic diagram of a modification of the sample scanner of FIG. 7 used in obtaining a metrology.

Nonetheless, assembling a metrology "on-the-fly" from a scan of an interferometric image provides the best opportunity for real-time analysis of a sample. A real-time metrology can be obtained using a slit wheel 910 in conjunction with slit 705 as shown in FIG. 9. Slit wheel 910 includes eight circumferential and evenly distributed radial slits 911–918. Scan drive 707 drives slit wheel 910 via mechanical link 921 in a counterclockwise direction as indicated by arrow 923.

Radial slits 911–918 are circumferentially spaced so that exactly one radial slit overlaps slit 705 at any one time. With slit wheel 910 oriented as shown in FIG. 9, slit 912 overlaps slit 705. The area of overlap defines a pixel window 931 which moves along slit 705 in the direction indicated by arrow 933. As slit 912 moves past slit 705, slit 913 moves in a position to overlap slit 705.

Slit wheel 910 should rotate fast enough for the entire interferometric sample image to be scanned. The continuous spinning of scanning prism 701 causes the interferometric sample image to move transversely of slit 705 while one of the radial slits, e.g., slit 912, moves longitudinally relative to slit 705. If, during the time it takes slit 912 to pass slit 705, the image is moved more than the width of slit 705, then there will be portions of the image that are never viewed by pixel window 931. Thus, slit wheel 910 should rotate so that at least one radial slit passes slit 705 for each slit-width of movement of the image relative to slit 705.

Each slit 911–918 is long enough to overlap completely the width of slit 705 anywhere along its length. Each slit 911–918 has the same width as slit 705. Thus, pixel window 931 is a diffraction-limited square. The interferometric sample image, as scanned by pixel window 931, is the input to sample transducer 115. The output of sample transducer 115, i.e., sample signal SS, represents the interferometric sample image on a pixel-by-pixel basis. Accordingly, when slit wheel 910 is used, sample signal SS permits the interferometric sample image to be reconstructed. The reconstructed interferometric sample image can be used to characterize the form of the location of interest.

Sample signal SS is a serial representation of the interferometric sample image corresponding to a selected location. Formatting sample signal SS into blocks, with each block corresponding to one sweep of slit 705 by one of the radial slits 911–918 provides a raster representation of the interferometric sample image at the location of interest. Sample signal SS can be processed in a variety of ways so that the metrology data it represents are presented in a concise and useful format. For example, each block of formated signal SS can be recorded to represent the changes relative to the previous block in fringe locations rather than absolute fringe locations. The resulting signal represents the metrology of the location of interest independent of its absolute position on sample 201. This form of the data can be most useful when comparing metrologies for different locations or between metrologies for a sample location and a corresponding location on exemplar 203.

When data is encoded in the form of changes between blocks, the changes represent local slopes of fringes. Each fringe represented in a block can be expressed by a linear approximation $y = kx + c$, where k is the slope and c is a displacement along the y direction. Successive fringes can be distinguished by the value of c. This suggests that signal SS can be converted to a string of data in the forms of slope values and displacement values, with the slopes representing local tangents to fringes and the displacement values representing spacing between fringes. Finally, the slope and displacement data can be replaced by changes in slope and changes in displacement from block to block. Such a representation would characterize the form of a location independent of its orientation and absolute position for comparison with other locations which might include similar defects or features at different orientations. Absolute position and absolute orientation can be reconstructed as desired from the start position of the scan.

Another way to obtain a metrology, not using slit wheel 910, is to use a quad detector or other means to maintain alignment of fringes and slit 705 while monitoring the alignment to provide slope data for the fringes. The relative motion of slit and image required for mutual alignment can involve rotating frame 703, and thus slit 705, or rotating the image, for example using a dove prism. Frame 703 or the dove prism can be optically encoded to provide a reading of alignment position, which corresponds to slope data. The quad detector would have an area on the order of that of slit 705 and be arranged to receive the same portion of the image viewed by slit 705. The output of the quad detector would be non-zero whenever a fringe is not aligned with slit 705 and the non-zero would be used to drive the alignment means until alignment is achieved. This approach yields a series of fringe detections along with slope data for each fringe detected. This information can also provide linear approximations of the form $y=kx+c$ for the fringes. Thus, permitting compact data storage and efficient reconstruction of interferometric image of interest.

Another alternative is to trace fringes while monitoring the tracing procedure. A quad detector can be used to track the alignment of a fringe with slit 705 and force the desired alignment to be maintained. Alternatively, changes in the output of sample signal SS when slit wheel 910 is used can be used to turn a dove prism to reorient the interferometric sample image with slit 705. Instead of a single slit, multiple slits could be used. For example, three pixel windows can be used. A center pixel window is used to trace a fringe. Two outer pixel windows provide correction signals when either views the fringe. This arrangement is analogous to that used in three-beam laser pick-up systems for compact discs. An output signal reflecting changes in alignment indicates form independent of absolute orientation and absolute position. This facilitates comparison with other features and defects.

In another embodiment, a CCD imager is used to store an interferometric sample image. The stored image is then vectorized into a compact data format for transmission, storage and reconstructions. Since the defect location process greatly limits the area of the wafer that must be analyzed, it can be cost effective to use more time-intensive CCD imaging for the metrology. Taking a CCD image of the interferometric image instead of the sample directly emphasizes form over reflectivity. Use of the reflectivity filtering techniques described above further enhances the fringes. The fringes can then be characterized by their size, shape, orientations, and inter-fringe spacing and gradient sign. The data format can be a series of commands required for a plotter or other device to reconstruct the fringes. Intermediate intensities and fringe thicknesses can be ignored in characterizing the sample. Thus, the interferometric imaging approach eliminates irrelevant and distraction information for the purposes of creating a metrology.

The foregoing procedures are alternative methods of encoding an interferometric image. However, it is not generally apparent whether a fringe represents a higher or lower level than a neighboring fringe. To resolve this ambiguity, a second interferometric image can be used. This second image can be obtained subsequently using a single beam imaging system by tilting the sample. Alternatively, an imaging system can employ two beams at slightly different angles relative to the sample. The differences between the interferometric images can be made small so that there is no ambiguity of correspondence between the fringes of one image and the other. Pairs of interference fringes move closer together when the gradient that they represent corresponds to the direction of tilt and move farther apart when the gradient is opposed to the tilt. This gradient information can be encoded along with the form data for the fringes. For example, a data format might include slope data indicating the local tangent of a fringe, spacing data indicating spacing relative to a neighboring fringe, and gradient direction data indicating the gradient direction from the neighboring fringe to the subject fringe.

Where the two interferometric images used to deduce height data are generated by two laser beams with different angles of incidence at the sample, the interferometric images can be examined sequentially. This can be done simply by scanning one interferometric image and then the other. However, it is preferably to analyze the two images concurrently to permit real-time metrologies. To this end, the two beams can have different frequencies or the same frequency but different polarization. The imager output can be split into two branches. One branch can be filtered to obtain one interferometric image and the other branch can be filtered to yield the other interferometric image.

The interferometric image of the first branch can be directed along beam path 125 to scanning prism 701 (see FIG. 7) and the interferometric image of the second branch can be directed along beam path 139, using appropriately arranged mirrors. In this configuration, the outputs of sample transducer 115 and exemplar transducer 121 represent the two interferometric images of the sample.

Each transducer output is in the form of a pulse train. The variable of interest is the duration between pairs of successive pulses. For example, where the duration between one pair of successive pulses in the exemplar transducer output is greater than the duration between a corresponding pair of pulses in the sample transducer output, this can indicate that the fringe corresponding to the latter pulse (in both pulse trains) represents a greater height than the earlier pulse. This relationship could be reversed, but it is the same for all pairs of pulses for a given configuration.

The duration information can be converted to amplitude information by using the first pulse to trigger the charging of a capacitor and the second pulse to stop the charging of the capacitor, as in a sample-and-hold arrangement. This conversion is performed on the outputs of both transducers 115 and 121. The resulting signals are then compared, e.g., using a differential amplifier. The instantaneous sign of the differential amplifier output then provides the height data to be correlated with the fringe data.

In all these metrology approaches, the distinctiveness of fringes can be enhanced using reflectivity filtering. Low spatial frequency reflectivity filtering can be performed on a region-by-region basis and high spatial frequency filtering can be performed using feedback from sample transducer 115.

As is apparent from the foregoing, the present invention provides an enhanced quality inspection system, as well as options for modification, variation and extension. In particular, a metrology extension is delineated above. These and other modifications and variations are provided for by the present invention, the scope of which is limited only by the following claims.

What is claimed is:

1. A system comprising:
   a sample analyzer for providing a sample signal, said sample analyzer including an sample imager for providing a real-time interferometric sample image from a sample, said sample analyzer including sample image conversion means for converting said interferometric sample image to said sample signal, said sample image conversion means including a sample image scanner for providing a sample scan by scanning said interferometric sample image;
   exemplar signal means for providing an exemplar signal corresponding to an interferometric exemplar image for an exemplar for said sample;
   controller means for coordinating the actions of said sample analyzer and said exemplar signal means so that concurrent values of said sample signal and said exemplar signal respectively represent corresponding spatial positions on said sample and said exemplar, said controller means being coupled to said sample analyzer and said exemplar signal means; and
   comparator for providing a comparison signal representing discrepancies in the form of said sample from the form of said exemplar, said comparator being coupled to said sample analyzer for receiving said sample signal and to said exemplar signal means for receiving said exemplar signal.

2. The system of claim 1 wherein said conversion means includes a sample transducer for converting said sample scan into said sample signal.

3. The system of claim 1 wherein said exemplar signal means includes an exemplar imager for providing a real-time interferometric exemplar image from an exemplar and exemplar conversion means for converting said exemplar image to said exemplar signal.

4. The system of claim 3 wherein said exemplar signal means also includes means for receiving an exemplar signal generated from digitally stored data.

5. The system of claim 1 further comprising a position memory for storing defect position data, said controller means including position monitoring means for monitoring the position on said sample corresponding to the current value of said comparison signal, said position memory having a data port coupled to said position monitoring means for receiving data therefrom, said position memory means having a write enable port coupled to said comparator for receiving said comparison signal therefrom so that current position data is stored in said memory when said comparison signal indicates a discrepancy in said sample from said exemplar.

6. The system of claim 5 wherein said comparator means also provides phase data representing the sign and duration of discrepancies between said sample signal and said exemplar signal, said comparator means being coupled to said controller means for transferring said phase data thereto so that said phase data can be stored in said position memory in conjunction with said position data.

7. A method comprising the steps of:
   obtaining an interferometric image to produce a sample scan;
   converting said sample scan to a sample signal;
   generating a comparison signal by comparing said sample signal to an exemplar signal corresponding to a scan of an interferometric image for said sample object;
   monitoring the position on said sample object corresponding to the current value of said comparison signal; and
   storing the position of said sample object corresponding to the current value of said sample signal and said exemplar signal so as to identify the location of possible discrepancies between said sample object and said exemplar.

8. The method of claim 7 wherein said exemplar signal is obtained by obtaining an interferometric exemplar image of an exemplar object, scanning said exemplar image and converting the resulting exemplar scan into said exemplar signal.

9. A system comprising:
   imager means for providing interferometric images, each of said interferometric images being a spatial distribution of intensity, said imager means including laser means for illuminating a sample object and for illuminating an exemplar object and means for interfering light from said laser means reflected from said sample object with light reflected from said exemplar object to produce said interferometric image;
   translation means for moving said sample object and said exemplar object relative to said imager means so that object regions of said sample object can be successively illuminated currently with corresponding exemplar regions of said exemplar object, said translation means maintaining said sample object and said exemplar object in a predetermined registration position relative to each other so that each of said interferometric images provides a comparison of one of said object regions with a corresponding one of said exemplar regions;
   scanning means for providing scans including at least one scan of each of said interferometric images, said scans being temporal distributions of intensity; and
   transducer means for converting each of said scans into signals characterizing said spatial distributions of intensity, each of said signals representing a comparison of one of said object regions with a corresponding one of said exemplar regions.

10. A system comprising:
    imager means for providing an interferometric image, said interferometric image being a spatial distribution of intensity, said imager means including laser means for illuminating a sample object and for illuminating a reference object and means for interfering light from said laser means reflected from said sample object with light reflected from said reference object to produce said interferometric image, said laser means including beam-splitting means for splitting a laser beam from said laser means so that it can separately illuminate said sample object and said reference object and so that a portion of the resulting reflections can be diverted away from said laser means and toward said scanning means, said imager means further including intensity means for controlling the intensity of the light output from said laser means and attenuator means for attenuating light transmitted between said beam-splitting means and said reference object, said imager means having sample sensor means for measuring the overall reflectivity of said sample object, said sample sensor means being coupled to said laser means for regulating the intensity of said laser output to maintain the intensity of the reflection from said sample object within a predetermined range, said sample sensor means also being coupled to said attenuator means so as to maintain the intensity of the component of said interferometric image resulting from reflection from said reference object within a predetermined intensity range;

scanning means for providing a scan of said interferometric image, said scan being a temporal distribution of intensity; and transducer means for converting said scan into a signal characterizing said spatial distribution of intensity.

11. The quality inspection system of claim 10 further comprising phase means for generating phase data, said phase means including replica means for generating a replica of said comparison signal, digitizing means for generating digital phase data representation of the duration of each interval during which said opposite logic level is maintained in said replica, said controller means directing said digital phase data to said data input means of said memory means so that said phase data is stored in said data input means while said write enable means is enabled.

12. A quality inspection system comprising:
(1) a sample imager for providing an interferometric sample image, said sample imager including:
  (1a) a laser source for providing a laser beam,
  (1b) intensity means for controlling the intensity of said laser beam,
  (1c) beam-splitting means for providing an incident sample beam and an incident reference beam along respective trajectories by transmitting one of said incident beams and reflecting the other,
  (1d) reference plane means for providing a reflected reference beam by reflecting said incident reference beam towards said beam-splitting means with minimal phase distortion,
  (1f) reference lens means for focussing said incident reference beam near said reference plane means,
  (1e) attenuator means for variably attenuating said incident reference beam and said reflected reference beam with minimal phase distortion, said attenuator means including attenuator input means for receiving a control signal for determining the instantaneous attenuation to be applied by said attenuator means,
  (1g) sample lens means for focussing said incident sample beam near an exposed surface of a sample so that said sample can provide a reflected sample beam by reflecting said incident sample beam, said reflected sample beam interfering with said reflected reference beam at said beam-splitting means to produce said interferometric sample image,
  (1h) sample sensor means for providing a first intensity control signal to said intensity means so adjust the intensity of said laser beam so that the overall intensity of said reflected sample beam is maintained within a predetermined range, said sample sensor means including a sample sensor optically coupled to said sample,
  (1i) reference sensor means for providing a first attenuation control signal representing the intensity of said reflected reference beam, said reference sensor means including a reference sensor optically coupled to said reference plane means,
  (1j) differential amplifier means for comparing said first intensity control signal with said first attenuation control signal to produce a second attenuation control signal, said differential amplifier means being coupled to said attenuator means for transmitting said second attenuation control signal thereto;

(2) an exemplar imager for providing an interferometric exemplar image of an exemplar, said exemplar imager including elements corresponding to those defined above for said sample imager, said exemplar imager sharing said laser source with said sample imager;

(3) stage means for carrying said sample and said exemplar so that their relative position and orientation is fixed, said stage means providing for the relative movement of said sample relative to said sample imager so that said interferometric sample image reflects different regions of said sample at different times, said stage means concurrently providing for the relative movement of said exemplar relative to said exemplar imager so that said interferometric exemplar image reflects different regions of said exemplar at different times and so that at any given time said interferometric sample image and said interferometric exemplar image correspond to corresponding respective regions of said sample and said exemplar, said stage means including stage drive means, said stage means including stage position monitoring means for providing stage position data representing the current position of said stage relative to said sample imager;

(4) scan means for providing a sample scan in the form of a scan of said interferometric sample image and an exemplar scan in the form of a scan of said interferometric exemplar image, said scan means including:
  (4a) a sample frame with a sample slit, said sample slit having a width on the order of one wavelength characterizing said laser beam, said sample slit having a length at least several times greater than its width,
  (4b) a exemplar frame with a exemplar slit, said exemplar slit having substantially the same dimensions as said sample slit,
  (4c) scanning prism means for sweeping said interferometric sample image relative to said sample slit so that said sample scan is generated in the form of a time-varying intensity passed by said sample slit and for sweeping said interferometric exemplar image relative to said exemplar slit so that said exemplar scan is generated in the form of a time-varying intensity passed by said exemplar slit, said scanning prism means being optically coupled to said sample imager for receiving said interferometric sample image therefrom and being optically coupled to said sample slit for sweeping said interferometric sample image relative thereto, said scanning prism means being optically coupled to said exemplar imager for receiving said interferometric exemplar image therefrom and being optically coupled to said exemplar slit for sweeping said interferometric exemplar image relative thereto, said scanning prism means including scanning drive means for rotating said scanning prism to that it sweeps images projected therethrough, (4d) scan monitor means for providing scan position data by monitoring the rotational position of said scanning prism;

(5) a sample transducer means for providing a binary sample signal and a second intensity control signal for said sample imager, said sample transducer means including:

(5a) a sample photo-multiplier for providing an analog sample signal, said photo-multiplier, said sample photo-multiplier optically coupled to said sample slit for receiving said sample scan therefrom, (5b) sample signal threshold means for thresholding said analog sample signal to provide said binary sample signal so that analog sample signal values above a threshold setting are assigned one logic level in said binary sample signal and so that analog sample signal values below that threshold setting are assigned the opposite logic level, (5c) sample signal intensity means for providing a second intensity control signal to said intensity means of said sample imager, said second intensity control signal corresponding to the intensity of said sample scan since the most recently passed dark fringe, said sample signal intensity means being coupled to said intensity control means so that the maximum intensity of said sample scan is maintained within a predetermined scan intensity range;

(6) an exemplar transducer for providing a binary exemplar signal, said sample transducer including elements corresponding to those defined above for said exemplar transducer, said transducer elements being coupled among themselves and to said exemplar imager in a manner corresponding to the couplings defined above for said exemplar transducer;

(7) comparator means for providing a binary comparison signal having one logic level representing times when the intensity patterns of said sample scan and a scan represented by an binary exemplar signal are matching and the opposite logic level when said scans are not matching;

(8) virtual exemplar means for receiving an exemplar signal not representing a current scan of an exemplar on said stage means;

(9) mode means for providing, in the alternative, for a real exemplar mode and a virtual exemplar mode so that:

(9a) when in said real exemplar mode, said comparator is coupled for receiving a binary exemplar signal from said exemplar transducer, and (9b) when in said virtual exemplar mode, said comparator is coupled for receiving a binary exemplar signal from said virtual exemplar means;

(10) memory means for storing stage position and scan position data, said memory means including:

(10a) memory for storing data, (10b) data input means for receiving data, (10c) write enable means for storing data received at said data input means only when enabled, said write enable means being coupled to said comparator means to receive said binary comparison signal therefrom said that said write enable means is enabled upon an transition to said opposite logic level, (10d) read means for transmitting data stored is said memory in response to a read input signal; and

(11) controller means for coordinating the actions of the above-recited components, said controller means providing said stage position data and said scan position data to said data input means of said memory means so that the data stored in said memory represents positions on said sample which differ in form from corresponding positions on said exemplar.

* * * * *